United States Patent [19]

Kataoka et al.

[11] Patent Number: 5,547,912
[45] Date of Patent: Aug. 20, 1996

[54] SOLID CATALYST COMPONENT FOR POLYMERIZING OLEFINS AND CATALYST CONTAINING THE SAME

[75] Inventors: Takuo Kataoka; Kenji Goto, both of Kanagawa, Japan

[73] Assignee: Toho Titanium Co., Ltd., Chigasaki, Japan

[21] Appl. No.: 380,979

[22] Filed: Jan. 31, 1995

[30] Foreign Application Priority Data

Jan. 31, 1994 [JP] Japan .................................. 6-027344
Jun. 23, 1994 [JP] Japan .................................. 6-164495
Jun. 23, 1994 [JP] Japan .................................. 6-164496

[51] Int. Cl.$^6$ ...................................................... B01J 31/38
[52] U.S. Cl. ........................... 502/154; 502/103; 502/115; 502/116; 502/127; 502/158; 526/123.1
[58] Field of Search ..................................... 502/103, 115, 502/116, 127, 154, 158

[56] References Cited

U.S. PATENT DOCUMENTS

| | | | |
|---|---|---|---|
| 4,315,835 | 2/1982 | Scata' | 252/429 B |
| 4,535,069 | 8/1985 | Shimizu et al. | 502/115 |
| 4,816,433 | 3/1989 | Terano et al. | 502/127 |
| 5,034,361 | 7/1991 | Job et al. | 502/9 |
| 5,112,927 | 5/1992 | Hara et al. | 526/124 |
| 5,147,839 | 9/1992 | Fujita et al. | 502/119 |

FOREIGN PATENT DOCUMENTS

| | | |
|---|---|---|
| 0032294 | 7/1981 | European Pat. Off. . |
| 0093494 | 11/1983 | European Pat. Off. . |
| 0171155 | 2/1986 | European Pat. Off. . |
| 0350170 | 1/1990 | European Pat. Off. . |
| 0537858 | 4/1993 | European Pat. Off. . |
| 0576411 | 12/1993 | European Pat. Off. . |

*Primary Examiner*—Shrive Beck
*Assistant Examiner*—Timothy H. Meeks
*Attorney, Agent, or Firm*—Oblon, Spivak, McClelland, Maier & Neustadt, P.C.

[57] ABSTRACT

A solid catalyst component for polymerizing olefins, which can provide a streoregular polymer having a low density of 0.900 to 0.906 g/ml at a high yield and a low RDS and which can prepare the polymer containing less fine powders. The solid catalyst component is prepared using substances (a) to (d) and optionally substance (e):

(a) a dialkoxymagnesium represented by $Mg(OR^1)_2$, wherein R represents a straight chain or branched chain alkyl group or an aryl group;

(b) an aluminium compound represented by $Al(OR^2)_n X^1_{3-n}$, wherein $R^2$ represents a straight chain or branched chain alkyl group; $X^1$ represents a halogen atom, and n is 0 or an integer of 1 to 3;

(c) titanium tetrachloride;

(d) a diester of dicarboxylic acid; and (e) a dimethyl polysiloxane.

12 Claims, No Drawings

SOLID CATALYST COMPONENT FOR POLYMERIZING OLEFINS AND CATALYST CONTAINING THE SAME

FIELD OF THE INVENTION

The present invention relates to a solid catalyst component for polymerizing olefins and a catalyst containing the solid catalyst component. More specifically, it relates to a high performance solid catalyst component and a catalyst containing the solid catalyst component which shows an excellent polymerization activity when used in polymerization of propylene, especially, by a slurry method and which can provide a stereoregular polymer having a density of from 0.900 to 0.906 g/ml at a high yield while suppressing the formation of fine powdery polymer.

BACKGROUND OF THE INVENTION

There have been made many proposals on solid catalyst components containing a titanium halides, a magnesium compound and an electron donor compound as essential components, and polymerization of olefins in the presence of a catalyst comprising such a solid catalyst component, an organic aluminium compound and a silicone compound.

Solid catalyst components comprising a dialkoxymagnesium and titanium tetrachloride as primary starting materials, and catalysts for polymerization of olefins which comprise such a solid catalyst component, an organic aluminium compound and a silicone compound are also known as described in, for example, JP-A-63-3010 (the term "JP-A" as used herein means an unexamined published Japanese patent application), JP-A- 1-221405, JP-A-1-315406, JP-A-3-227309, JP-A-3-70711, and JP-A-4-8709.

Further, solid catalyst components containing an aluminium halide, a magnesium compound and a titanium halide as essential components, and catalysts containing such a solid catalyst component, an organic aluminium compound and as the third component, an organic acid ester or a silicone compound are known. For example, JP-A-55-161807 discloses a catalyst comprising (i) a composition obtained by pulverizing magnesium chloride, an organic acid ester, a halogenated hydrocarbon and an aluminium halide together and then carrying out heat treatment with titanium tetrachloride, (ii) an organic aluminium compound, and (iii) an organic acid ester; and JP-A- 61-31402 discloses a catalyst comprising (i) a solid catalyst component obtained by reacting a reaction product of an aluminium halide and a silicone compound with a magnesium compound and then reacting with a titanium halide and an ester of phthalic acid, (ii) an organic aluminium compound and (iii) a silicone compound.

Furthermore, solid catalyst components containing an alkoxyaluminium compound, a magnesium compound and a titanium halide as essential components, and catalysts for polymerization of olefins which contain such a solid catalyst component, an organic aluminium compound and as the third component, an organic acid ester or a silicone compound are also known. For example, JP-A-57-145104 discloses a catalyst component obtained by pulverizing magnesium chloride, an organic acid ester and an alkoxyaluminium compound together and then carrying out heat treatment with titanium tetrachloride; and JP-A-1-245002 discloses a catalyst comprising (i) a solid catalyst component obtained by bringing diethoxymagnesium into contact with titanium tetrachloride, followed by addition of an trialkoxyaluminium and then reacting with phthalic dichloride, (ii) an organic aluminium compound, and (iii) an epoxy-p-menthane compound.

These solid catalyst components and catalysts as described above have been developed as a result of studies for attaining high catalytic activity in polymerization of propylene so that the amount of the solid catalyst component can be minimized and the step of removing a catalyst residue (e.g., chlorine and titanium) remaining in a resulting polymer can be omitted, for improving the yield of a stereoregular polymer, or for improving durability of the catalytic activity for polymerization, and they provide good results for the respective objects. However, none of these catalysts can produce stereoregular polymers having a density of from 0.900 to 0.906 g/ml without lowering the yield of stereoregular polymers insoluble in a polymerization solvent as used in polymerization of olefins, particularly polymerization of propylene, according to the slurry method.

In the case where olefins, particularly propylene are polymerized by the slurry method in the presence of the aforesaid highly active catalyst, the resulting polymer has a high stereoregularity and is obtained in a high yield as compared with the case where a catalyst comprising a conventional titanium trichloride type solid catalyst component, an organic aluminium compound and an electron donor compound is used. However, the density of the resulting polymer tends to be higher than 0.906 g/ml, giving rise to various problems, e.g., breaking in rapid rolling rate and deterioration in transparency of a film product molded by a BOPP molding.

It has been known that the density of the resulting polymer can be controlled to some extents by lowering the polymerization temperature or introducing a small amount of ethylene as a comonomer into the polymerization system of olefins (particularly propylene) in the presence of the aforesaid highly active catalyst. In case of the slurry method, however, an undesirable phenomenon occurs that a low molecular weight polymer which is soluble in a polymerization solvent is formed at a high rate, and in the polymerization of propylene or copolymerization of propylene and ethylene, an atactic polypropylene which has an extremely poor stereoregularity is generated at a high rate. The atacticity can be evaluated in terms of the content of soluble portions of the resulting polymer or copolymer in a polymerization solvent, which is hereafter referred to "RDS" (the content of reactor diluent solubles).

Increase of the RDS in the slurry polymerization gives rise to problems with respect to the production cost of a polymer and the stability in operation because a reactor and a pipeline are stained, and an extraction step is required after separation of the particles of a resulting polymer from a polymerization solvent. Further, generation of fine powders contained in the resulting polymer, particularly those having a particle size of 100 micron or less, tend to cause clogging in a pipeline in the polymerization process, and other problems in the step of separation and drying of the polymer.

SUMMARY OF THE INVENTION

An object of the present invention is to provide a solid catalyst component for polymerization of olefins, which can provide a stereoregular polymer having a density of from 0.900 to 0.906 g/ml at a low RDS and yet at a high yield, with suppressing formation of fine powders, and also to provide a catalyst using the solid catalyst component.

The object of the present invention can be attained by a solid catalyst component (A) for polymerizing olefins, which is prepared using substances (a) to (d) and optionally substance (e):

(a) a dialkoxymagnesium represented by $Mg(OR^1)_2$ wherein $R^1$ represents a straight chain or branched chain alkyl group or an aryl group;

(b) an aluminium compound represented by $Al(OR^2)_n X^1_{3-n}$ wherein $R^2$ represents a straight chain or branched chain alkyl group, $X^1$ represents a halogen atom, and n is 0 or an integer of 1 to 3;

(c) titanium tetrachloride;

(d) a diester of aromatic dicarboxylic acid; and (e) a dimethyl polysiloxane.

The solid catalyst component (A) of the present invention is preferably used as an ingredient of a catalyst for polymerization of olefins, together with ingredients (B) and (C):

(B) an organic aluminium compound represented by $R^3_p AlX^2_{3-p}$, wherein $R^3$ represents a straight chain or branched chain alkyl group, $X^2$ represents a halogen atom, a hydrogen atom, or an alkoxy group, and p is a real number of 1 to 3; and (C) a silicone compound represented by $R^4_q Si(OR^5)_{4-q}$ wherein $R^4$ represents a straight chain or branched chain alkyl group, a cycloalkyl group, an aryl group, or a vinyl group, and the plurality of $R^4$ groups may be the same or different; $R^5$ represents a straight chain or branched chain alkyl group, and q is 0 or an integer of 1 to 3.

DETAILED DESCRIPTION OF THE INVENTION

The dialkoxymagnesium (substance (a)) represented by $Mg(OR^1)_2$ preferably has a straight chain or branched chain alkyl group having up to 10 carbon atoms, more preferably 2 to 4 carbon atoms, or an aryl group for $R^1$. Examples of substance (a) includes diethoxymagnesium, dipropoxymagnesium, dibutoxymagnesium, and diphenoxymagnesium, with diethoxymagnesium being preferred.

The dialkoxymagnesium, which can be used preferably, is at least one dialkoxymagnesium species having from 1 to 3 carbon atoms in the alkoxy moiety thereof and has a granular or powdered form, the particles of which may have an irregular shape or a spherical shape. In using spherical particles of diethoxymagnesium with a narrower particle size distribution, the resulting powdered polymer will have a more satisfactory particle shape and a narrower particle size distribution. As a result, the polymer powder as produced has improved handling properties, and troubles attributed to fine particles, such as obstruction, would be eliminated.

The spherical diethoxymagnesium particles as above referred to do not necessarily need to be true spheres, and ellipsoidal or potato-like particles may also be used. The terminology "spherical" as used herein may be quantified as a longer axis diameter (l) to shorter axis diameter (w) ratio (l/w) of not more than 3, preferably from 1 to 2, and still preferably from 1 to 1.5.

The dialkoxymagnesium to be used has an average particle size of from 1 to 200 μm, preferably from 5 to 150 μm.

In the case of spherical diethoxymagnesium, it has an average particle size of from 1 to 100 μm, preferably from 5 to 50 μm, more preferably from 10 to 40 μm. It is preferable to use particles having a sharp size distribution with a small proportion of fine of coarse particles. More specifically, particles containing not more than 20%, preferably not more than 10%, of fine particles of 5 μm or smaller and not more than 10%, preferably not more than 5%, of coarse particles of 100 μm or greater. Such a particle size distribution corresponds to ln ($D_{90}/D_{10}$) of not more than 3, preferably not more than 2, wherein $D_{90}$ and $D_{10}$ represent a cumulative 90% diameter and a cumulative 10% diameter, respectively, of a cumulative particle size distribution depicted from the small diameter size.

The above-mentioned dialkoxymagnesium does not always need to be present as a starting material in the preparation of solid catalyst component (A). For example, it may be prepared in situ from metallic magnesium and an alcohol in the presence of a catalyst, e.g., iodine at the time of preparing solid catalyst component (A).

The aluminium compound represented by $Al(OR^2)_n X^1_{3-n}$ (substance (b)) preferably has a straight chain or branched chain alkyl group having up to 10 carbon atoms, more preferably up to 5 carbon atoms, for $R^2$, such as trihalogenated aluminium, halogenated alkoxyaluminium and trialkoxyaluminium. Examples of trihalogenated aluminium include aluminium trichloride, aluminium tribromide and aluminium triiodide, with aluminium trichloride being preferred. Examples of halogenated alkoxyaluminium includes diethoxychloroaluminium, ethoxydichloroaluminium, diisopropoxychloroaluminium, isopropoxydichloroaluminium, dibutoxychloroaluminium, and butoxydichloroaluminium, with ethoxydichloroaluminium, diisopropoxychloroaluminium, and isopropoxydichloroaluminium being prepared. Examples of trialkoxyaluminium include trimethoxyaluminium, triethoxyaluminium, tripropoxyaluminium, triisopropoxyaluminium, tributoxyaluminium, and triisobutoxyaluminium, with triethoxyaluminium and triisopropoxyaluminium being preferred. These aluminium compounds may be used independently or as admixture thereof.

The aromatic dicarboxylic diester substance (d) is preferably a phthalic diester. The ester moiety thereof is preferably a straight chain or branched chain alkyl group having up to 15 carbon atoms, more preferably 2 to 12 carbon atoms. Examples of phthalic diester include dimethyl phthalate, diethyl phthalate, di-n-propyl phthalate, di-isopropyl phthalate, di-n-butyl phthalate, di-iso-butyl phthalate, ethylmethyl phthalate, butylethyl phthalate, methyl(iso-propyl) phthalate, ethyl-n-propyl phthalate, ethyl-n-butyl phthalate, di-n-pentyl phthalate, di-iso-pentyl phthalate, di-n-hexyl phthalate, di-n-heptyl phthalate, di-n-octyl phthalate, bis(2-methylhexyl) phthalate, bis(2-ethylhexyl) phthalate, di-n-nonyl phthalate, di-iso-decyl phthalate, bis(2,2-dimethylheptyl) phthalate, n-butyl(iso-hexyl) phthalate, ethyl(iso-octyl) phthalate, n-butyl(iso-octyl) phthalate, n-pentyl(n-hexyl) phthalate, n-pentyl(iso-hexyl) phthalate, iso-pentyl(n-heptyl) phthalate, n-pentyl(iso-octyl) phthalate, n-pentyl(iso-nonyl) phthalate, iso-pentyl(n-decyl) phthalate, n-pentyl(n-undecyl) phthalate, iso-pentyl(iso-hexyl) phthalate, n-hexyl(iso-octyl) phthalate, n-hexyl(iso-nonyl) phthalate, n-hexyl(n-decyl) phthalate, n-heptyl(iso-octyl) phthalate, n-heptyl(iso-nonyl) phthalate, n-heptyl(neo-decyl) phthalate, and iso-octyl(iso-nonyl) phthalate. At least one of them is used. Of these, diethyl phthalate, di-n-propyl phthalate, di-n-butyl phthalate, di-iso-butyl phthalate, and bis(2-ethylhexyl) phthalate are preferred. These phthalic diesters may be used independently or as admixture thereof.

The dimethyl polysiloxane (e) (substance (e)) is an optional component constituting the solid catalyst component (A) of the present invention and is preferably a polymer silicone compound represented by the following formula

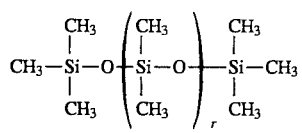

wherein r is 1,000 to 30,000. The dimethyl polysiloxane has a viscosity of 5 to 1,000 centistokes, preferably 10 to 500 centistokes, at a room temperature.

The solid catalyst component (A) of the present invention can be prepared by contacting the substance (a), the substance (b), titanium tetrachloride referred to as the "substance (c)") and the substance (d); or the substance (a), the substance (b), the substance (c), the substance (d) and the substance (e), in the presence or absence of an inert organic solvent. For easy operation, the processing is preferably carried out in the presence of the solvent. The inert organic solvent used includes saturated hydrocarbon such as hexane, heptane and cyclohexane; aromatic hydrocarbon such as benzene, toluene, xylene and ethylbenzene; and halogenated hydrocarbon such as o-dichlorobenzene, methylene chloride, carbon tetrachloride, and dichloroethane. Among these, aromatic hydrocarbons having a boiling point of 90° to 150° C. are preferably used.

The used amount of the respective substances are 0.01 to 10 g, preferably 0.05 to 2.0 g for the substance (b), 0.1 to 200 ml, preferably 0.5 to 100 ml for the substance (c), 0.01 to 1.0 g, preferably 0.1 to 0.5 g for the substance (d), and 0.05 to 5.0 ml, preferably 0.1 to 1.0 ml for the substance (e), each based on 1 g of the substance (a). The amount of the inert organic solvent is not specifically limited, and it is preferably from 1 to 10 ml per 1 ml of the substance (c) for easy operation.

Each of these substances (a) to (e) can be brought into contact at once or piece by piece. The contact of the respective substances is carried out in a vessel equipped with a stirrer under an inert gas atmosphere in a moisture-free condition while stirring. The contact temperature may be a relatively low temperature close to room temperature in the case of simply contacting by way of stirring and mixing the substances or in case of dispersing or suspending the substances in an inert organic solvent. In case of reacting the substances after contact to obtain a reaction product, the temperature is preferably from 40° to 130° C. If the temperature is less than 40° C., the reaction does not sufficiently proceed, and the resulting solid catalyst component may not exhibit sufficient catalytic performances. If the temperature is higher than 130° C., the solvent is markedly evaporated so that the reaction becomes unstable. The reaction time is preferably 1 minute or more, more preferably 10 minutes or more, and most preferably 30 minutes or more.

Preferred contact orders of the respective substances in the present invention are as follows:

(1) the substances (a), (b), (c) and (d) are contacted at the same time;

(2) the substance (c) is contacted to a product obtained by contacting the substances (a), (b), (c) and (d);

(3) the substance (d) is contacted to a product obtained by contacting the substances (a), (b) and (c) in advance;

(4) the substance (d) is contacted to a product obtained by contacting the substances (a), (b) and (c) in advance, and then the substance (c) is further contacted;

(5) the substance (b) is contacted to a product obtained by contacting the substances (a), (c) and (d) in advance;

(6) the substance (b) is contacted to a product obtained by contacting the substances (a), (c) and (d) in advance, and then the substance (c) is further contacted, (7) the substance (b) is contacted to a product obtained by contacting the substances (a), (c) and (d) in advance, and then the substances (b) and (c) are further contacted;

(8) the substances (b) and (c) are contacted to a product obtained by contacting the substances (a), (b), (c) and (d) in advance;

(9) the substances (a), (b), (c), (d) and (e) are contacted at the same time;

(10) the substance (c) is contacted to a product obtained by contacting the substances (a), (b), (c), (d) and (e);

(11) the substances (d) and (e) are contacted to a product obtained by contacting the substances (a), (b) and (c) in advance;

(12) the substances (d) and (e) are contacted to a product obtained by contacting the substances (a), (b) and (c) in advance, and then the substance (c) is further contacted;

(13) the substance (b) is contacted to a product obtained by contacting the substances (a), (c), (d) and (e) in advance;

(14) the substance (b) is contacted to a product obtained by contacting the substances (a), (c), (d) and (e) in advance, and then the substance (c) is further contacted;

(15) the substance (b) is contacted to a product obtained by contacting the substances (a), (c), (d) and (e) in advance, and then the substances (b) and (c) are further contacted; and

(16) the substances (b) and (c) are contacted to a product obtained by contacting the substances (a), (b), (c), (d) and (e).

The contact condition in the case of contacting the substance (b) and/or the substance (c) in the later stage is preferably that the substance (b) and/or the substance (c) are added as they are, or diluted by the inert organic solvent described above and then added (the latter being preferably) to the product, and allowed to stand at a temperature of 40° to 130° C. for 1 minute or more, preferably 10 minutes or more, and more preferably 30 minutes or more. A ratio of the substance (b) to the substance (c), when both are added to the product, may be the same or different as that in the contact and reaction at the former stage (to form the product). The product obtained by the contact and reaction in the former stage may be washed with the inert organic solvent described above, and again contacted with the substance (b) and/or the substance (c).

It is preferred to wash the thus prepared solid catalyst component (A) of the present invention in the inert organic solvent such as heptane, whereby unreacted substances can be removed. With or without drying, the washed component (A) is mixed with the organic aluminium compound (B) and the silicone compound (C) as described in detail below, to thereby form the catalyst for polymerizing olefins of the present invention.

The organic aluminium compound (B) which is used together with the solid catalyst component (A) of the present invention to form the catalyst for polymerization of olefins is represented by $R^3_p AlX^2_{3-p}$, wherein $R^3$ represents a straight chain or branched chain alkyl group preferably having up to 15 carbon atoms, more preferably up to 5 carbon atoms, $X^2$ represents a halogen atom, a hydrogen atom, or an alkoxy group preferably up to 4 carbon atoms, and p is a real number of 1 to 3. Examples of the organic aluminium compound (B) (referred to as "component (B)") include trialkylaluminiums such as triethylaluminium and triisobutylaluminium; dialkylaluminium halides such as diethylaluminium chloride and dibutylaluminium chloride;

alkylaluminium sesquihalides such as ethylaluminium sesquichloride and butylaluminium sesquichloride; alkylaluminium alkoxides such as diethylaluminium ethoxide and dibutylaluminium butoxide; alkylaluminium hydrides such as diethylaluminium hydride, dibutylaluminium hydride and ethylaluminium hydride; and a mixture thereof. Of these, triethylaluminium and triisobutylaluminium are preferred.

The silicone compound represented by $R^4_q Si(OR^5)_{4-q}$ (referred to as "component (C)") is another ingredient to be used together with the components (A) and (B) to form the catalyst for polymerization of olefins. In the formula, $R^4$ is a straight chain or branched chain alkyl group preferably having up to 20 carbon atoms, more preferably up to 12 carbon atoms, a cycloalkyl group, an aryl group or a vinyl group, and the plurality of $R^4$ may be the same as or different, and $R^5$ represents a straight chain or branched chain alkyl group preferably having up to 10 carbon atoms, more preferably up to 5 carbon atoms. Examples of component (C) include phenyl alkoxysilanes, alkyl alkoxysilanes, phenyl alkyl alkoxysilanes, cycloalkyl alkoxysilanes, and cycloalkyl alkyl alkoxysilanes. To concretely exemplify the component (C) described above, preferred are trimethyl methoxysilane, trimethyl ethoxysilane, tri-n-propyl methoxysilane, tri-n-propyl ethoxysilane, tri-n-butyl methoxysilane, tri-iso-butyl methoxysilane, tri-t-butyl methoxysilane, tri-n-butyl ethoxysilane, tricyclohexyl methoxysilane, tricyclohexyl ethoxysilane, dimethyl dimethoxysilane, dimethyl diethoxysilane, di-n-propyl dimethoxysilane, di-iso-propyl dimethoxysilane, di-n-propyl diethoxysilane, di-iso-propyl diethoxysilane, di-n-butyl dimethoxysilane, di-iso-butyl dimethoxysilane, di-t-butyl dimethoxysilane, di-n-butyl diethoxysilane, n-butyl methyl dimethoxysilane, bis(2-ethylhexyl) dimethoxysilane, bis(2-ethylhexyl) diethoxysilane, dicyclohexyl dimethoxysilane, dicyclohexyl diethoxysilane, dicyclopentyl dimethoxysilane, dicyclopentyl diethoxysilane, cyclohexyl cyclopentyl dimethoxysilane, cyclohexyl methyl dimethoxysilane, cyclohexyl methyl diethoxysilane, cyclohexyl ethyl dimethoxysilane, cyclohexyl isopropyl dimethoxysilane, cyclohexyl ethyl diethoxysilane, cyclopentyl ethyl diethoxysilane, cyclopentyl isopropyl dimethoxysilane, cyclohexyl(n-pentyl) dimethoxysilane, cyclopentyl isobutyl dimethoxysilane, cyclohexyl(n-pentyl) diethoxysilane, cyclohexyl(n-propyl) dimethoxysilane, cyclohexyl(n-butyl) dimethoxysilane, cyclohexyl(n-propyl) diethoxysilane, cyclohexyl(n-butyl) diethoxysilane, diphenyl dimethoxysilane, diphenyl diethoxysilane, phenyl methyl dimethoxysilane, phenyl methyl diethoxysilane, phenyl ethyl dimethoxysilane, phenyl ethyl diethoxysilane, cyclohexyl dimethyl methoxysilane, cyclohexyl dimethyl ethoxysilane, cyclohexyl diethyl methoxysilane, cyclohexyl diethyl ethoxysilane, 2-ethylhexyl trimethoxysilane, 2-ethylhexyl triethoxysilane, methyl trimethoxysilane, methyl triethoxysilane, ethyl trimethoxysilane, ethyl triethoxysilane, n-propyl trimethoxysilane, n-propyl triethoxysilane, iso-propyl trimethoxysilane, iso-propyl triethoxysilane, n-butyl trimethoxysilane, iso-butyl trimethoxysilane, t-butyl trimethoxysilane, n-butyl triethoxysilane, cyclohexyl trimethoxysilane, cyclohexyl triethoxysilane, cyclopentyl trimethoxysilane, cyclopentyl triethoxysilane, vinyl trimethoxysilane, vinyl triethoxysilane, 2-ethylhexyl trimethoxysilane, 2-ethylhexyl triethoxysilane, phenyl trimethoxysilane, phenyl triethoxysilane, tetramethoxy silane and tetraethoxy silane. Of these, di-n-propyl dimethoxysilane, di-iso-propyl dimethoxysilane, di-n-butyl dimethoxysilane, di-iso-butyl dimethoxysilane, di-t-butyl dimethoxysilane, di-n-butyl diethoxysilane, t-butyl trimethoxysilane, dicyclohexyl dimethoxysilane, dicyclohexyl diethoxysilane, cyclohexyl dimethoxysilane, cyclohexyl methyl diethoxysilane, cyclohexyl ethyl dimethoxysilane, cyclohexyl ethyl diethoxysilane, dicyclopentyl dimethoxysilane, dicyclopentyl diethoxysilane, cyclopentyl methyl diethoxysilane, cyclopentyl ethyl diethoxysilane, tetraethoxy silane, and cyclohexyl cyclopentyl dimethoxysilane are preferably used. These silicone compounds may be used independently or as admixture thereof.

In preparation of the polymerization catalyst of the present invention, the component (B) is used in an amount of 1 to 1000 moles, preferably 50 to 500 moles per mole of the titanium atom contained in the solid catalyst component (A), and the component (C) is used in an amount of 0.0020 to 2 moles, preferably 0.01 to 0.5 mole per mole of the component (B). The solid catalyst component (A) used in the catalyst of the present invention generally has a Ti content of 0.5 to 15% by weight and preferably 1 to 7% by weight.

Olefins which are homopolymerized or copolymerized using the catalyst of the present invention includes ethylene, propylene, 1-butene, 4-methyl-1-pentene, and the like, and it is particularly preferably propylene.

The polymerization may be carried out by a slurry polymerization, a bulk polymerization or a gas phase polymerization. The catalyst of the present invention is particularly suitable for the slurry polymerization carried out in the presence of an inert organic solvent such as hexane and heptane, and an olefin monomer is used by way of dissolving in the organic solvent. Hydrogen can be used as a molecular weight controller in the polymerization. The polymerization temperature is generally 200° C. or lower, preferably 100° C. or lower, and the polymerization pressure is generally 10 MPa or less, preferably 5 MPa or less, and more preferably 2.5 MPa or less.

For ensuring the improvements in catalytic activity and stereoregularity and particle properties of the polymer produced, it is preferable to conduct pre-polymerization prior to substantial polymerization. Monomers to be pre-polymerized include not only ethylene and propylene but other monomers, such as styrene and vinylcyclohexane.

By the use of the catalyst of the present invention, in polymerization of olefins, particularly polymerization of propylene, a stereoregular polymer having a low density of 0.900 to 0.906 g/ml can be produced stably at a low RDS of 3% or less (preferably 2% or less). Further, the yield of the polymer per unit amount of the catalyst is high, that is, the catalyst has a high polymerization activity and exhibits excellent performances in terms of catalytic life and reduction of a fine powder content in the resulting polymer.

The present invention will be explained below with reference to the Examples.

EXAMPLE 1

Preparation of solid catalyst component:

10 g of diethoxymagnesium, 1.5 g of aluminium trichloride and 90 ml of toluene were put in a 500-ml round flask equipped with a stirrer, which had been fully purged with nitrogen gas, and they were mixed to prepare a suspension. Then, 22 ml of titanium tetrachloride (maintained at a room temperature) was added therein, and the temperature was increased to 80° C. while stirring to carry out a reaction. Next, 3.0 ml of di-n-butyl phthalate was added, and the temperature was further increased to 110° C. to continue the reaction for 2 hours. Thereafter, a supernatant of the resulting suspension was removed, and the residue was washed three times with 88 ml of toluene at 75° C. Subsequently, 89 ml of toluene and 22 ml of titanium tetrachloride were added thereto, and processing was carried out at 100° C. for 1.5 hour while stirring, followed by washing eight times with 83 ml of heptane at 40° C., whereby a solid catalyst component having a Ti content of 3.8% by weight and an Al content of 0.5% by weight was obtained.

Preparation of catalyst and polymerization of propylene:

700 ml of n-heptane was put in a 1800-ml stainless steel autoclave equipped with a stirrer, which had been fully dried with nitrogen gas and replaced with propylene gas. Under the propylene gas atmosphere, 2.10 mmol of triethylaluminium, 0.21 mmol of phenyl triethoxysilane and 0.084 mmol (in terms of Ti) of the above-prepared solid catalyst component were put therein in the autoclave, whereby a catalyst was prepared. Thereafter, a propylene pressure was adjusted to 0.2 MPa, and preliminary polymerization of propylene was carried out at 20 ° C. for 30 minutes with stirring. 30 ml of hydrogen gas was then introduced in the autoclave, and the propylene pressure in the system was adjusted to 0.7 MPa to continue the polymerization at 70° C. for 2 hours. The pressure, which decreased as the polymerization of propylene proceeded, was supplemented by continuously supplying only propylene to keep the pressure constant during the polymerization. The polymer thus produced was filtered off and dried under reduced pressure to obtain a solid polymer.

Measurement of properties of catalyst:

A filtrate separated from the solid polymer was concentrated to obtain the polymer dissolved in the solvent, and the amount of the polymer was designated as (A), while the amount of the solid polymer was designated as (B). Further, the solid polymer obtained was extracted in boiled n-heptane for 6 hours to obtain a polymer insoluble in n-heptane, and the amount thereof was designated as (C). The properties of the catalyst were calculated from these values (A), (B) and (C), as described below.

Polymerization activity (Y) per unit amount of solid catalyst component:

Y=[(A)+(B)](g)/amount of solid catalyst component (g)

Content of reactor diluent solubles (RDS):

(RDS)=(A)(g)/[(A)+(B)](g)

Yield (t-II) of a whole crystalline polymer:

(t-II)=(C)(g)/[(A)+(B)](g)

Further, a density (ρ), a melt index (MI) (measured by the method according to JIS K7210) and a bulk density (BD) of the resulting solid polymer were measured, and the results are shown in Table 1, together with the above-measured properties of the catalyst.

EXAMPLE 2

Preparation of solid catalyst component:

10 g of diethoxymagnesium and 90 ml of toluene were put in a 500-ml round flask equipped with a stirrer, which had been fully replaced with nitrogen gas, to prepare a suspension. Then, 20 ml of titanium tetrachloride was added therein, and the temperature was increased to 70° C. while stirring to carry out the reaction. Next, 4.0 ml of di-i-octyl phthalate was added, and the temperature in the system was further increased to 110° C. to continue the reaction for 2 hours. After completion of the reaction, a supernatant of the resulting suspension was removed, and the residue was washed three times with 88 ml of toluene at 75° C. Thereafter, 80 ml of toluene, 2.0 g of aluminium trichloride and 30 ml of titanium tetrachloride were added, and the reaction was carried out at 105° C. for 2 hours with stirring, followed by washing eight times with 80 ml of heptane at 40° C., whereby a solid catalyst component having a Ti content of 3.4% by weight and an Al content of 0.7% by weight was obtained.

Preparation of catalyst and polymerization of propylene:

Propylene was polymerized in the same manner as that in Example 1, except that phenyl triethoxysilane was replaced with dicyclohexyl dimethoxysilane, and the results are shown in Table 1.

EXAMPLE 3

Preparation of solid catalyst component:

10 g of diethoxymagnesium, 0.8 g of aluminium trichloride and 90 ml of toluene were put in a 500-ml round flask equipped with a stirrer, which has been fully purged with nitrogen gas, to prepare a suspension. Then, 22 ml of titanium tetrachloride was added therein, and the temperature was increased to 80° C. while stirring to carry out the reaction. Next, 2.8 ml of di-i-octyl phthalate was added, and the temperature was further increased to 110° C. to continue the reaction for 2 hours. After completion of the reaction, a supernatant of the resulting suspension was removed, and the residue was washed twice with 88 ml of toluene at 75° C. Thereafter, 0.8 g of aluminium trichloride, 89 ml of toluene and 22 ml of titanium tetrachloride were added, and the processing was carried out at 100° C. for 1.5 hour while stirring, followed by washing eight times with 83 ml of heptane at 40° C., whereby a solid catalyst component having a Ti content of 2.9% by weight and an Al content of 0.8% by weight was obtained.

Preparation of catalyst and polymerization of propylene:

Propylene was polymerized in the same manner as that in Example 1, except that phenyl triethoxysilane was replaced with cyclohexyl methyl dimethoxysilane, and the results are shown in Table 1.

COMPARATIVE EXAMPLE 1

A solid catalyst component was prepared and polymerization of propylene was carried out in the same manner as in Example 1, except that aluminium trichloride was not used. The results obtained are shown in Table 1.

COMPARATIVE EXAMPLE 2

A solid catalyst component was prepared in the same manner as in Example 1, except that aluminium trichloride was not used and the amount of di-n-butyl phthalate was changed to 2.0 ml. The resulting solid catalyst component had a Ti content of 5.5% by weight.

Using the solid catalyst component, polymerization of propylene was carried out in the same manner as in Example 1, and the results are shown in Table 1.

TABLE 1

|  | Ex. 1 | Ex. 2 | Ex. 3 | Comp. Ex. 1 | Comp. Ex. 2 |
| --- | --- | --- | --- | --- | --- |
| Polymerization activity (Y) | 11,500 | 13,000 | 26,000 | 11,700 | 10,700 |
| RDS* | 1.0 | 0.9 | 0.8 | 0.5 | 4.5 |
| Yield of whole crystalline polymer (t-II) | 96.1 | 95.4 | 95.5 | 98.2 | 92.6 |
| Density of polymer (ρ: g/ml) | 0.9052 | 0.9048 | 0.9045 | 0.9080 | 0.9049 |
| Melt index of polymer | 3.7 | 3.5 | 1.9 | 2.2 | 4.0 |

TABLE 1-continued

|  | Ex. 1 | Ex. 2 | Ex. 3 | Comp. Ex. 1 | Comp. Ex. 2 |
| --- | --- | --- | --- | --- | --- |
| (MI: g/10 min) Bulk density of polymer (BD: g/ml) | 0.41 | 0.40 | 0.39 | 0.40 | 0.38 |

(* in n-heptane)

It is seen from the results shown in Table 1 that the use of the solid catalyst component of the present invention produces polypropylene having a density of not more than 0.906 g/ml at a low RDS of 3% or less.

EXAMPLE 4

Preparation of solid catalyst component:

10 g of diethoxymagnesium, 1.5 g of triethoxyaluminium and 90 ml of toluene were put in a 500-ml round flask equipped with a stirrer, which had been fully purged with nitrogen gas, to prepare a suspension. Then, 30 ml of titanium tetrachloride was added therein, and the temperature was increased to 80° C. while stirring to carry out the reaction. Next, 3.0 ml of di-n-butyl phthalate was added, and the temperature was further increased to 110° C. to continue the reaction for 2 hours. After completion of the reaction, a supernatant of the resulting suspension was removed, and the residue was washed three times with 90 ml of toluene at 75° C. Thereafter, 90 ml of toluene and 30 ml of titanium tetrachloride were added, and the processing was carried out at 100° C. for 2 hours while stirring, followed by washing eight times with 80 ml of heptane at 40° C., whereby a solid catalyst component having a Ti content of 5.5 by weight and an Al content of 0.8% by weight was obtained.

Preparation of catalyst and polymerization of propylene:

Propylene was polymerized in the same manner as that in Example 1, except that phenyl triethoxysilane was replaced with cyclohexyl methyl dimethoxysilane. The results are shown in Table 2.

EXAMPLE 5

A solid catalyst component was prepared in the same manner as that in Example 4, except that triethoxyaluminium was replaced with triisopropoxyaluminium. Using the solid catalyst component, polymerization of propylene was carried out in the same manner as in Example 4, and the results are shown in Table 2.

EXAMPLE 6

A solid catalyst component was prepared in the same manner as that in Example 4, except that triethoxyaluminium was replaced with ethoxydichloroaluminium. Using the solid catalyst component polymerization of propylene was carried out in the same manner as in Example 4, and the results are shown in Table 2.

EXAMPLE 7

Preparation of solid catalyst components:

10 g of diethoxymagnesium, 1.5 g of triisopropoxyaluminium and 90 ml of toluene were put in a 500-ml round flask equipped with a stirrer, which had been fully purged with nitrogen gas, to prepare a suspension. 30 ml of titanium tetrachloride was added therein, and the temperature was increased to 80° C. with stirring to carry out the reaction. Next, 3.5 ml of di-i-octyl phthalate was added, and the temperature was further increased 110° C. to continue the reaction for 2 hours. After completion of the reaction, a supernatant of the resulting suspension was removed, and the residue was washed with 90 ml of toluene at 75° C. Thereafter, 0.5 g of ethoxydichloroaluminium, 90 ml of toluene and 30 ml of titanium tetrachloride were added, and the processing was carried out at 100° C. for 2 hours while stirring, followed by washing eight times with 80 ml of heptane at 40° C., whereby a solid catalyst component having a Ti content of 4.2% by weight and an Al content of 0.8% by weight was obtained.

Preparation of catalyst and polymerization of propylene:

Propylene was polymerized in the same manner as that in Example 4, except that 0.0053 mmol in terms of Ti of the above-prepared solid catalyst component Ti was used, and the results are shown in Table 2.

COMPARATIVE EXAMPLE 3

A solid catalyst component was prepared and polymerization of propylene was carried out in the same manner as in Example 4, except that triethoxyaluminium was not used. The results obtained are shown in Table 2.

TABLE 2

|  | Ex. 4 | Ex. 5 | Ex. 6 | Ex. 7 | Comp. Ex. 3 |
| --- | --- | --- | --- | --- | --- |
| Polymerization activity (Y) | 24,200 | 26,100 | 28,900 | 25,700 | 24,500 |
| RDS* | 1.5 | 1.2 | 1.0 | 1.4 | 0.5 |
| Yield of whole crystalline polymer (t-II) | 95.0 | 95.3 | 95.4 | 94.8 | 98.5 |
| Density of polymer ($\rho$: g/ml) | 0.9050 | 0.9052 | 0.9048 | 0.9047 | 0.9078 |
| Melt index of polymer (MI: g/10 min) | 4.0 | 2.8 | 1.8 | 1.5 | 1.8 |
| Bulk density of polymer (BD: g/ml) | 0.40 | 0.41 | 0.40 | 0.40 | 0.40 |
| Ti content (wt %) | 5.5 | 5.2 | 3.5 | 4.2 | 2.5 |
| Al content (wt %) | 0.8 | 0.7 | 0.6 | 0.8 | — |

(* in n-heptane)

EXAMPLE 8

Preparation of solid catalyst component:

10 g of diethoxymagnesium, 1.5 g of aluminium trichloride and 90 ml of toluene were put in a 500-ml round flask equipped with a stirrer, which had been fully purged with nitrogen gas, to prepare a suspension. Then, 22 ml of titanium tetrachloride was added therein, and the temperature was increased to 80° C. while stirring to carry out the reaction. Next, 3.3 ml of di-n-butyl phthalate and 3.0 ml of dimethyl polysiloxane having a viscosity of 50 cst at room temperature were added, and the temperature was further increased to 110° C. to continue the reaction for 2 hours. After completion of the reaction, a supernatant of the resulting suspension was removed and the residue was washed three times with 88 ml of toluene at 75° C. Thereafter, 89 ml of toluene and 22 ml of titanium tetrachloride were added, and the processing was carried out at 100° C. for 1.5 hour while stirring, followed by washing eight times with 83 ml of heptane at 40° C., whereby a solid catalyst component having a Ti content of 3.3% by weight and an Al content of 0.5% by weight was obtained.

Preparation of catalyst and polymerization of propylene:

Using the above-prepared solid catalyst component, polymerization of propylene was carried out in the same manner as in Example 7, and the results are shown in Table 3.

EXAMPLE 9

Preparation of solid catalyst components:

10 g of diethoxymagnesium, 1.0 g of aluminium trichloride and 90 ml of toluene were put in a 500-ml round flask equipped with a stirrer, which had been fully purged with nitrogen gas, to prepare a suspension. Then, 20 ml of titanium tetrachloride was added therein, and the temperature was increased 50° C. while stirring to carry out the reaction. Next, 4.5 ml of di-i-octyl phthalate was added, and the temperature was added to continue the reaction for 2 hours. After completion of the reaction, a supernatant of the resulting suspension was removed, and the residue was washed three times with 88 ml of toluene at 75° C. Thereafter, 80 ml of toluene, 1.0 g of aluminiumchloride and 30 ml of titanium tetrachloride were added, and the reaction was carried out at 105° C. for 2 hours while stirring, followed by washing eight times with 80 ml of heptane at 40° C., whereby a solid catalyst component having a Ti content of 2.9% by weight and an Al content of 0.8% by weight was obtained.

Preparation of catalyst and polymerization of propylene:

Propylene was polymerized in the same manner as in Example 7, except that cyclohexyl methyl dimethoxysilane was replaced with diphenyl dimethoxysilane, and the results are shown in Table 3.

EXAMPLE 10

Preparation of solid catalyst component:

10 g of diethoxymagnesium, 0.8 g of aluminium trichloride and 90 ml of toluene were put in a 500-ml round flask equipped with a stirrer, which had been fully purged with nitrogen gas, to prepare a suspension. Thus, 22 ml of titanium tetrachloride was added therein, and the temperature was increased to 80° C. while stirring to carry out the reaction. Next, 4.8 ml of di-i-octyl phthalate was added, and the temperature was further increased to 110° C., and then 6.0 ml of dimethyl polysiloxane having a viscosity of 100 cst at room temperature was added to continue the reaction for 2 hours. After completion of the reaction, a supernatant of the resulting suspension was removed, and the residue was washed twice with 88 ml of toluene at 75° C. Thereafter, 0.8 g of aluminium chloride, 89 ml of toluene and 22 ml of titanium tetrachloride were added, and the processing was carried out at 100° C. for 1.5 hour while stirring, followed by washing eight times with 83 ml of heptane at 40° C., whereby a solid catalyst component having a Ti content of 2.5% by weight and an Al content of 0.8% by weight was obtained.

Preparation of catalyst and polymerization of propylene:

Using the above-prepared solid catalyst component, propylene was polymerized in the same manner as in Example 7, except that cyclohexyl methyl dimethoxy silane was replaced with cyclohexyl cyclopentyl dimethoxy silane, and the results are shown in Table 3.

COMPARATIVE EXAMPLE 4

A solid catalyst component was prepared and the polymerization of propylene was carried out in the same manner as in Example 8, except that aluminiumtrichloride and dimethyl polysiloxane were not used. The results obtained are shown in Table 3.

TABLE 3

| | Ex. 8 | Ex. 9 | Ex. 10 | Comp. Ex. 4 |
|---|---|---|---|---|
| Polymerization activity (Y) | 37,500 | 43,000 | 42,000 | 22,800 |
| RDS* | 0.7 | 0.5 | 0.5 | 1.0 |
| Yield of whole crystalline polymer (t-II) | 95.6 | 96.3 | 96.1 | 98.5 |
| Density of polymer (p: g/ml) | 0.9042 | 0.9051 | 0.9038 | 0.9075 |
| Melt index of polymer (MI: g/10 min) | 2.5 | 1.7 | 3.0 | 1.9 |
| Bulk density of polymer (BD: g/ml) | 0.41 | 0.38 | 0.38 | 0.40 0.36 |
| Content of fine powder (100 μ or less in diameter) | 1.0 | 1.5 | 1.5 | 9.0 5.5 |

(* in n-heptane)

EXAMPLE 11

Preparation of solid catalyst component:

10 g of diethoxymagnesiumand 90 ml of toluene were put in a 500-ml round flask equipped with a stirrer, which had been fully purged with nitrogen gas, to prepare a suspension. Then, 20 ml of titanium tetrachloride was added therein, and the temperature was increased to 50° C. while stirring to carry out the reaction. Next, 4.5 ml of di-i-octyl phthalate was added, and the temperature was further increased to 110° C., and then 4.0 ml of dimethyl polysiloxane having a viscosity of 50 cst at room temperature was added to continue the reaction for 2 hours. After completion of the reaction, a supernatant of the resulting suspension was removed, and the residue was washed three times with 88 ml of toluene at 75° C. Thereafter, 80 ml of toluene, 1.0 g of aluminium trichloride and 30 ml of titanium tetrachloride were added, and the reaction was carried out at 105° C. for 2 hours while stirring, followed by washing eight times with 80 ml of heptane at 40° C., whereby a solid catalyst component having a Ti content of 2.6% by weight and an Al content of 0.7% by weight was obtained.

Preparation of catalyst and polymerization of propylene:

20 ml of n-heptane was put in a 2000-ml stainless steel autoclave equipped with a stirrer, which had been fully dried with nitrogen gas and then purged with propylene gas. Under the propylene gas atmosphere, 1.32 mmol of triethylaluminium, 0.13 mmol of cyclohexyl methyl dimethoxysilane and 0.0033 mmol (in terms of Ti) of the above-prepared solid catalyst component were added therein, whereby a catalyst was prepared. Thereafter 1,400 ml of liquefied propylene was added therein, and the mixture was stirred at 20° C. for 5 minutes. 1500 ml of hydrogen gas was introduced with stirring, and then the temperature in the system was immediately increased to 70° C. to carry out the polymerization for 1 hour, whereby 224 g of polypropylene was obtained.

A polymerization activity, which was expressed by a polymer yield per g of the solid catalyst component in a polymerization time of 1 hour, was 37,300 g/g-cat. For evaluation of stereoregularity of the polymer obtained, a content of insoluble polymer after boiling in n-heptane for 6 hours was measured, and it was 95.5%. Further, it was found that the polymer obtained had a density of 0.9052, an average particle size of 400 μm, a bulk density of 0.42 g/ml, and a melt index of 9.4 g/10 min. Furthermore, the content of fine powder of 100 micron or less in diameter was 1.5% by weight.

As described above, when olefins, particularly propylene, are polymerized with the catalyst of the present invention, the catalic activity is sufficiently high, so that a residual amount of the catalyst present in the resulting polymer can be suppressed to a very low level, and accordingly, a residual chlorine amount in the resulting polymer can be reduced to an extent that a step of removing such contaminates can be omitted. A density of resulting stereoregular polypropylene can stably be controlled with in the range of 0.900 to 0.906 g/ml without changing a process parameter in a polymerization reaction to a large extent, and a polymer suited for a film or sheet formation can readily be produced. Further, in the case where the polymerization is carried out in the presence of the catalyst of the present invention, the content of fine powders in the resulting polymer can be reduced, and therefore, troubles on a process operation due to such fine powders can be prevented.

Since the RDS can be controlled very low, an posttreatment of a polymer produced by the slurry method and a refining process for a polymerization solvent used in the slurry method, can be simplified, resulting in cost reduction such as saving of energy in an operation. Further, the catalyst of the present invention has a long life with respect to the polymerization activity, enabling steady control of the polymerization process.

The solid catalyst component of the present invention can be prepared by a simple process without any specific additional equipments and exhibits a stable quality with a good reproducibility. Further, the solid catalyst component is advantageous because of its low production cost owing to use of inexpensive materials and a fast settling speed in a washing process as well as a small loss of solid materials during the process.

While the invention has been described in detail and with reference to specific embodiments thereof, it will be apparent to one skilled in the art that various changes and modification can be made therein without departing from the spirit and scope thereof.

What is claimed is:

1. A solid catalyst component (A) for polymerizing an olefin, which is prepared using substances (a) to (d):
   (a) a dialkoxymagnesium represented by $Mg(OR^1)_2$, wherein $R^1$ represents a straight chain or branched chain alkyl group or an aryl group;
   (b) an aluminum compound represented by $Al(OR^2)_n X^1_{3-n}$, wherein $R^2$ represents a straight chain or branched chain alkyl group; $X^1$ represents a halogen atom; and n is 0 or integer of 1 to 3;
   (c) titanium tetrachloride; and
   (d) a diester of aromatic dicarboxylic acid, wherein
      (c) or (b) and (c) are reacted with a product obtained by reacting (a), (b), (c) and (d), or
      (b) and (c) are reacted with a product obtained by reacting (a), (c) and (d).

2. The solid catalyst component (A) as in claim 1, wherein the substance (b) is a trihalogenated aluminium.

3. The solid catalyst component (A) as in claim 1, wherein the substance (b) is a halogenated alkoxyaluminium.

4. The solid catalyst component (A) as in claim 1, wherein the substance (b) is a trialkoxyaluminium.

5. A catalyst for polymerizing olefins, which comprises:
   (A) a solid catalyst component as defined in claim 1;
   (B) an organic aluminium compound represented by $R^3_p AlX^2_{3-p}$, wherein $R^3$ represents a straight chain or branched chain alkyl group, $X^2$ represents a hydrogen atom, a halogen atom, or an alkoxy group, and p is a real number of 1 to 3; and
   (C) a silicone compound represented by $R^4_q Si(OR^5)_{4-q}$ wherein $R^4$ is independently selected from a straight chain or branched chain alkyl group, a cylcloalkyl group, an aryl group, or a vinyl group, $R^5$ represents a straight chain or branched chain alkyl group, and q is 0 or an integer of 1 to 3.

6. The solid catalyst component as in claim 1, wherein the substance (c) or substance (b) are diluted by an inert organic solvent and then added to the product obtained by contacting the substances (a), (b), (c) and (d) in (i) or the substances (a), (c) and (d) in (ii).

7. A solid catalyst component (A) for polymerizing olefins, which is prepared using substances (a) to (e):
   (a) a dialkoxymagnesium represented by $Mg(OR^1)_2$, wherein $R^1$ represents a straight chain or branched chain alkyl group or an aryl group;
   (b) an aluminum compound represented by $Al(OR^2)_n X^1_{3-n}$, wherein $R^2$ represents a straight chain or branched chain alkyl group; $X^1$ represents a halogen atom; and n is 0 or integer of 1 to 3;
   (c) titanium tetrachloride;
   (d) a diester of aromatic dicarboxylic acid; and
   (e) a dimethyl polysiloxane, wherein
      (iii) (c) or (b) and (c) are reacted with a product obtained by reacting (a), (b), (c), (d) and (e), or
      (iv) (b) and (c) are reacted with a product obtained by reacting (a), (c), (d) and (e).

8. The solid catalyst component as in claim 7, wherein the substance (c) or substance (b) are diluted by an inert organic solvent and then added to the product obtained by contacting the substances (a), (b), (c), (d) and (e) in (iii) or the substances (a), (c), (d) and (e) in (iv).

9. The solid catalyst component (A) as in claim 7, wherein the substance (b) is a trihalogenated aluminum.

10. The solid catalyst component (A) as in claim 7, wherein the substance (b) is a halogenated alkoxyaluminum.

11. The solid catalyst component (A) as in claim 7, wherein the substance (b) is a trialkoxyaluminum.

12. A catalyst for polymerizing olefins, which comprises:
   (A) a solid catalyst component as defined in claim 7;
   (B) an organic aluminum compound represented by $R^3_p AlX^2_{3-p}$, wherein $R^3$ represents a straight chain or branched chain alkyl group, $X^2$ represents a halogen atom, a hydrogen atom, or an alkoxy group, and p is a real number of 1 to 3; and
   (C) a silicon compound represented by $R^4_q Si(OR^5)_{4-q}$ wherein $R^4$ is independently selected from a straight chain or branched chain alkyl group, a cycloalkyl group, an aryl group, or a vinyl group, $R^5$ represents a straight chain or branched chain alkyl group, and q is 0 or an integer of 1 to 3.

* * * * *